United States Patent [19]  [11]  4,137,456
Hogan  [45]  Jan. 30, 1979

[54] INFANT X-RAY EXAMINATION CRADLE SYSTEM

[75] Inventor: William F. Hogan, Woodbury, N.J.

[73] Assignee: Spectrum X-Ray Corporation, Westville, N.J.

[21] Appl. No.: 737,486

[22] Filed: Nov. 1, 1976

[51] Int. Cl.² .................. G01N 21/00; G01N 23/00
[52] U.S. Cl. ............................. 250/456; 250/439 P
[58] Field of Search .............. 250/439, 456; 269/322, 269/323

[56] References Cited

U.S. PATENT DOCUMENTS

| | | | |
|---|---|---|---|
| 3,215,834 | 11/1965 | Tayman | 250/439 R |
| 3,655,178 | 4/1972 | Vezina | 250/439 |
| 3,848,132 | 11/1974 | Foderaro | 250/456 |

Primary Examiner—Craig E. Church
Assistant Examiner—Thomas P. O'Hare
Attorney, Agent, or Firm—Paul & Paul

[57] ABSTRACT

An infant cradle or basket has upright basket ends and removable patient-support center panels of different lengths on which the infant is strapped and supported for X-ray examination. Beyond one of the basket ends is a motor or handcrank drive having a trunnion or pivot shaft on which the one basket end is mounted. Beyond the other basket end is a bearing support for a trunnion or pivot shaft. The basket is rotatable on its pivot shafts through 360°. Three different interchangeable mounting means are provided so that the rotatable infant basket may be attached either to a separately rotatable adult patient X-ray examination basket, or to an inclinable X-ray examination table top, or to a stationary X-ray examination table top.

7 Claims, 13 Drawing Figures

INFANT X-RAY EXAMINATION CRADLE SYSTEM

BACKGROUND OF THE INVENTION

This invention relates to rotatable cradles or baskets for receiving patients for full length X-ray examination, and in particular to a rotatable cradle or basket for receiving and holding infants for X-ray examination.

In my U.S. Pat. No. 3,757,129, granted Sept. 4, 1973, I describe an adult patient-receiving basket for an X-ray examination table having a motor drive for rotating the basket about its own longitudinal axis and moving the basket transversely on the X-ray examination table top. The table top is pviotal about its short or transverse axis so that the patient in the basket may be placed in various inclined positions ranging between horizontal and vertical. Moreover, since the X-ray table top is supported on pedestal elevator means located under the center portion of the table top, the table top and hence the baskets may be elevated and lowered.

The source of X-rays is positioned above the examination table top to project X-rays down through the table top onto an image plane located below. The image plane may be an image amplifier, or a photographic film, or any other suitable image-forming device. Thus, the examination table top is disposed between the source of X-rays and the image plane. The patient to be X-rayed is ordinarily strapped in the basket in full-length on-the-back position. The patient-support center panel of the basket is made of material which is transparent to X-rays. One example of such material is plywood.

SUMMARY OF THE INVENTION

An important object of the present invention is to provide a separately and independently rotatable cradle or basket for infant X-ray examination which may be attached to a rotatable and transversely movable adult patient-receiving basket of the type disclosed in my aforesaid U.S. patent, thereby to provide an infant-receiving basket capable of placing the infant in an extremely wide variety of positions for X-ray examination ranging from horizontal to vertical for all general radiography, fluoroscopy treatment, and special studies.

Another object is to provide a rotatable infant-receiving X-ray examination cradle or basket having a plurality of different types of interchangeable mounts so that the basket may be removably attached to either a rotatable adult-receiving X-ray examination basket, or to an inclinable X-ray examination table top, or to a stationary X-ray examination table top.

Another object is to provide an infant-receiving X-ray examination basket which may be left in position as a permanent installation or quickly and easily disassembled for convenient storage.

Another object is to provide an infant basket of the foregoing type which may be rotated through 360° with either a variable speed reversible D.C. motor drive or a mechanical hand crank.

While the infant cradle or basket described in the present application is adapted for interchangeable mounts, the desired versatility of angles of rotation, inclination and position are obtained when the infant-receiving basket is attached to an adult-receiving basket of the type described in my U.S. Pat. No. 3,757,129. This follows from the facts that the infant-receiving basket or cradle itself is rotatable through 360°, that the adult patient-receiving basket to which the infant cradle is attached is independently rotatable, that the adult basket is movable back-and-forth laterally relative to the X-ray examination table top, and that the X-ray examination table top is elevatable and tiltable. By rotating the adult patient-receiving basket about its lengthwise axis to a position 90° from its normal or horizontal position, the patient-supporting panel portion of the adult basket is placed in a substantially vertical position, to one side of the infant cradle. In this position, the X-rays from the source above the table top pass only through the infant and through the infant support panel. They do not pass through the support panel of the adult cradle. This avoids the impedance which the adult-cradle support panel would otherwise introduce into the path of the X-rays.

DETAILED DESCRIPTION OF THE PREFERRED EMBODIMENTS

The rotatable infant-receiving basket for X-ray examination of infants may, according to the present invention, be mounted in several different ways. Three different mounts are disclosed. One form of mount, namely, by suction feet, is suitable for attaching the infant-receiving basket to the flat surface of a stationary X-ray examination table top. This form of suction foot mounting is illustrated in FIGS. 1-7 of the application.

A second form of mounting is illustrated in FIGS. 8-11 in which the rotatable infant-receiving basket is attached to an adult-receiving basket which is independently rotatable, inclinable, elevatable and transversely movable. This form of infant-basket mounting is a preferred form in that it allows the infant to be examined from an extremely wide variety of positions.

Figure 12:
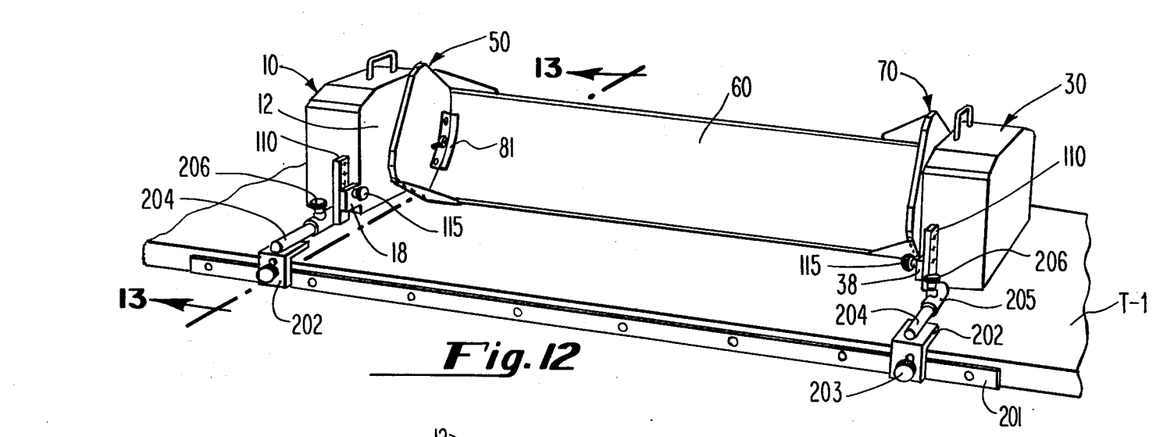
FIG. 12 is a view of the rotatable infant-receiving basket attached to a tiltable X-ray examination table top.
Figure 13:
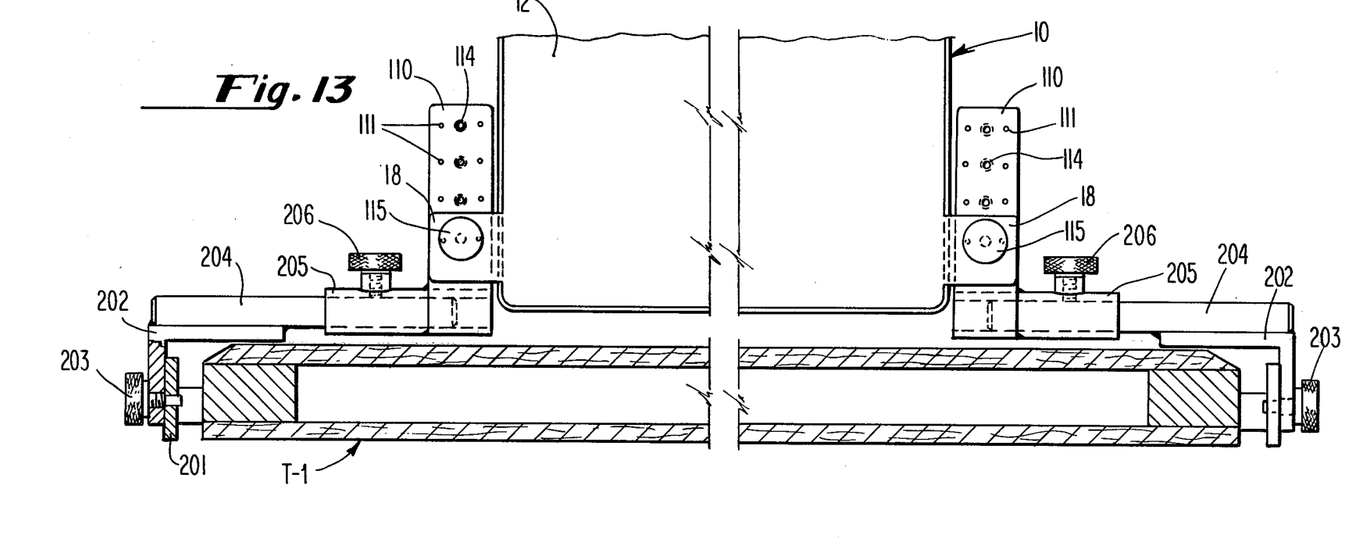
FIG. 13 is a view looking to the left along the line 13—13 of FIG. 12.

A third form of mounting is illustrated in FIGS. 12-13. This form of mounting is suitable for attaching the rotatable infant-receiving basket to a tiltable X-ray examination table top.

Figure 1:
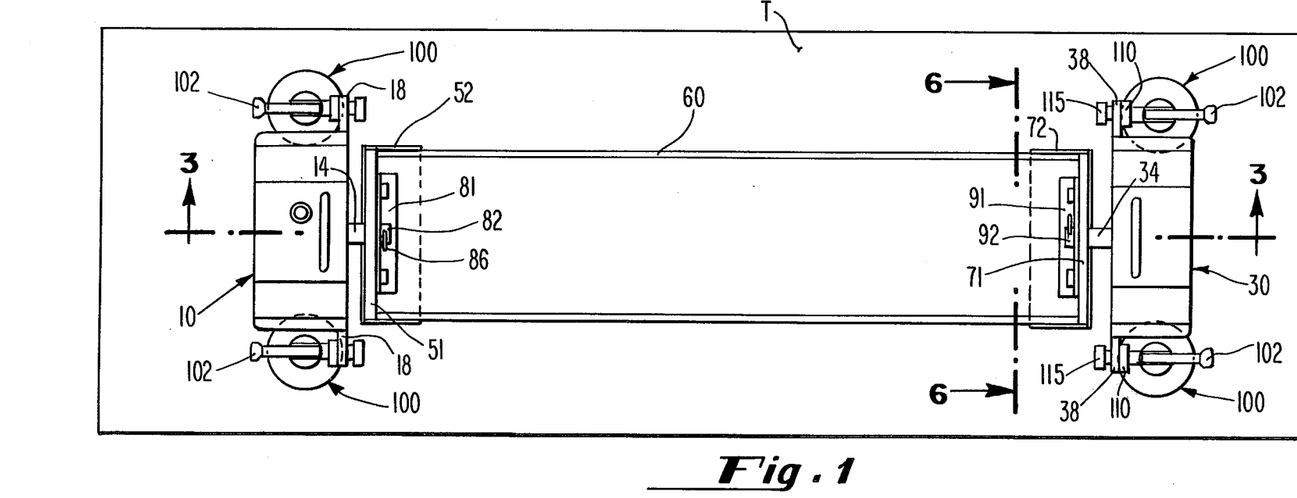
FIG. 1 is a top plan view of a rotatable infant-receiving basket mounted on a stationary X-ray examination table top.
Figure 2:
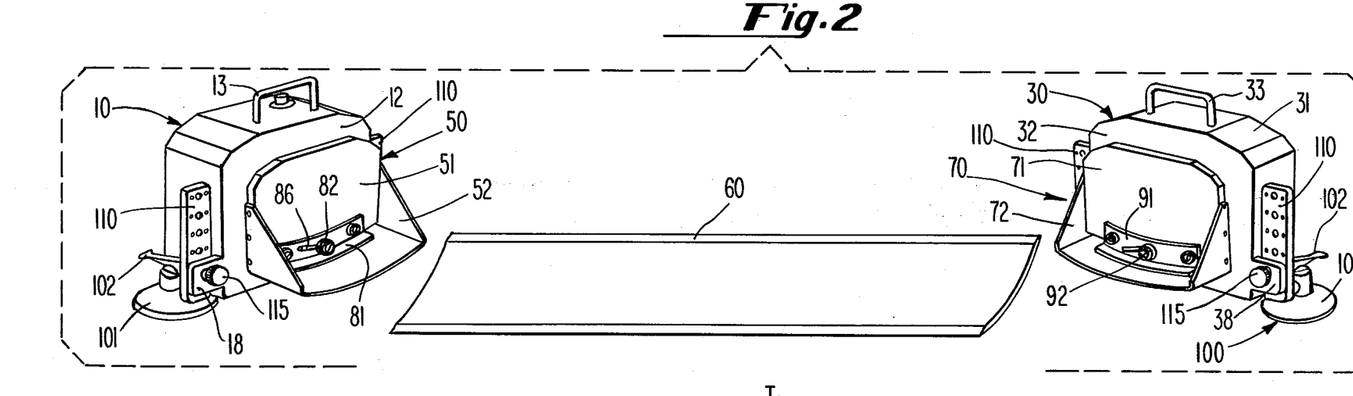
FIG. 2 is an exploded perspective view of the infant-receiving basket and its drive.

Referring now to FIGS. 1 and 2, the infant-receiving basket is there illustrated as attached by four suction feet 100 to the flat surface of the stationary X-ray examination table top T. The infant-receiving basket per se comprises three sections, namely, a head end section 50, a center infant patient-support panel 60, and a foot end section 70. The center infant-supporting panel 60 is arcuate or dished. It may preferably be made of plywood with a formica finish. It is available in several different lengths, such as 26, 36 and 40", to accommodate infants of different sizes.

Figures 3, 4, 5:
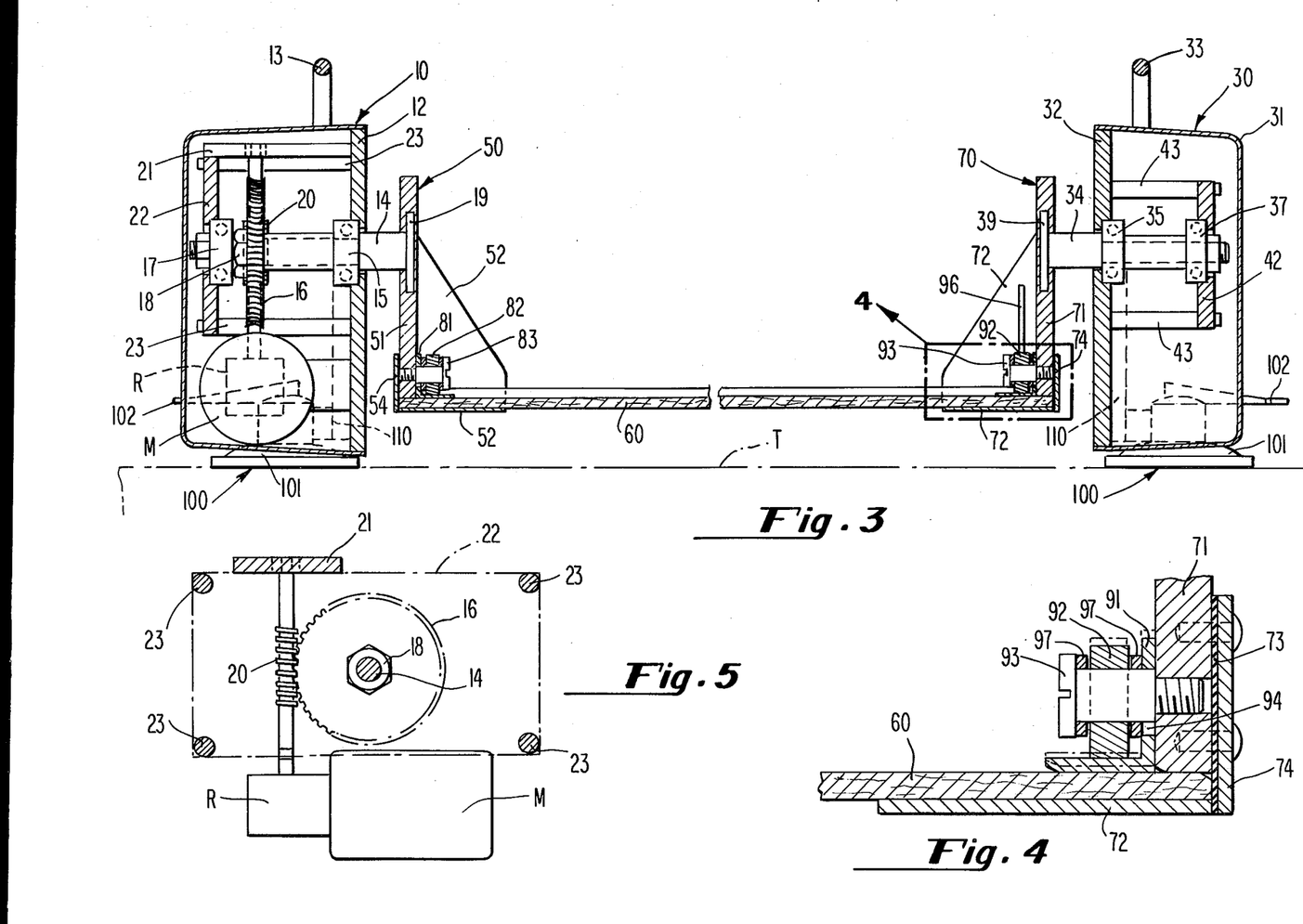
FIG. 3 is a side elevational view, in section, looking along line 3—3 of FIG. 1.
FIG. 4 is an enlarged detailed view of the end portion of the basket contained within the block identified 4 in FIG. 3.
FIG. 5 is an elevational end view looking along the line 5—5 of FIG. 3.

Each of the basket end sections 50 and 70 is supported on a trunnion or pivot shaft identified 14 and 34 in FIG. 1. The trunnion 14 at the head end is rotatable through 360° by either a hand crank or by a motor drive. Only the motor drive is illustrated in the present application. As seen in FIGS. 3 and 5, the motor drive is contained within housing 10. It includes a variable speed reversible D.C. motor M which drives a worm 20 and worm gear 16 through a gear reducer R. The worm shaft is supported at its upper end in a plate 21 within housing 10. The worm gear 16 is mounted on, and keyed or otherwise secured to the trunnion or pivot shaft 14. The pivot shaft 14 is journalled for rotation in bearings 15 and 17 supported in plates 12 and 22, respectively. Plate 12 is the cover plate of the housing 10. Plate 22 is within the housing 10 and is supported on four stand-off posts 23.

There is no motor drive at the other or foot end of the basket. The foot-end housing 30 contains only the pivot shaft 34 and suitable bearings 35 and 37 mounted in end plate 32 and interior plate 42, respectively. Interior plate 42 is supported by four stand-off posts 43.

Each of the trunnions or pivot shafts 14 and 34 has a flange at its outward end, identified 19 and 39, respectively. These flanges are secured to the basket end plates 51 and 71, respectively. Although not illustrated, each of the basket end plates 51 and 71 has a cover plate which is placed over the flange and then bonded to the end plate.

Secured, as by screws not shown, to opposite edges of each of the basket end plates 51 and 71, is a U-shaped end bracket identified 52 and 72, respectively. The upstanding sides of brackets 52, 72 are triangular in shape. The floor portions of the end brackets 52 and 72 support opposite ends of the patient-receiving center panels 60. To secure the panel ends firmly in the basket end sections 50 and 70, each of the basket end sections is provided with a clamp identified 81 and 91, respectively. These clamps are cam operated manually. Details of one of the clamps are shown in FIGS. 4 and 6.

FIG. 4 shows in enlarged detail that portion of the basket end section which is within phantom block 4 of FIG. 3. FIG. 6 is a view of the clamp 91 as viewed looking along the line 6—6 of FIG. 1. The U-shaped end bracket 72 is so positioned on the basket end plate 71 that space is left below the lower edge of plate 71 for receiving the incoming edge of the panel 60. To protect the edge of panel 60, a rubber bumper 73 is positioned as shown in FIG. 4 and held in place by retaining plate 74.

Figures 6, 7:
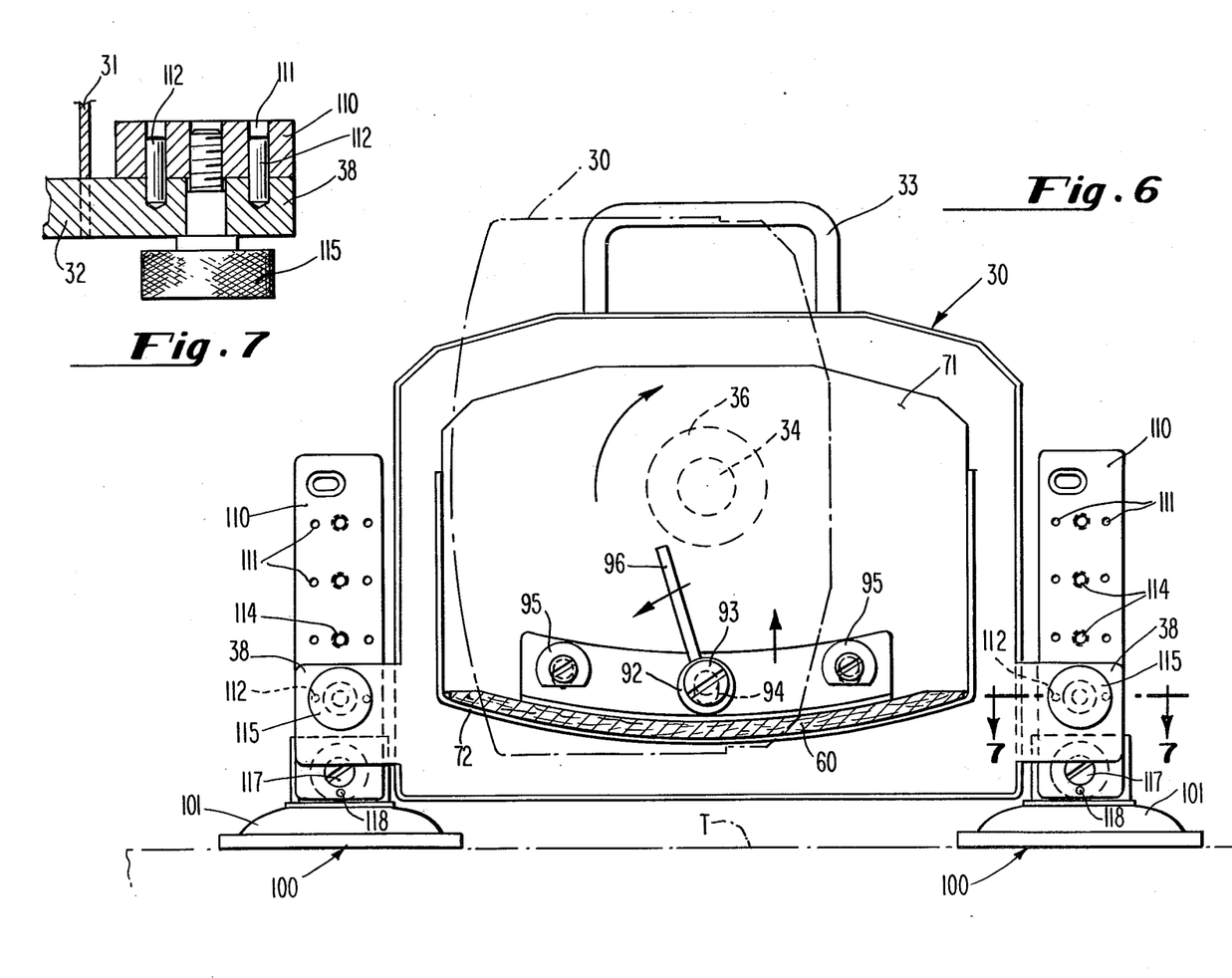
FIG. 6 is an elevational view looking to the right along the line 6—6 of FIG. 1.
FIG. 7 is a detailed view looking down along the line 7—7 of FIG. 6.

The clamp 91 is an angle member which, as seen in FIG. 6 is slidably secured to the face of basket end plate 71 by three shoulder screws which pass through vertical slots 94 in the clamp 91. The two side screws 95 (FIG. 6) are shoulder screws which abut against the face of plate 71. The center screw 93 is also a shoulder screw. This screw is seen in FIG. 4. This screw 93 has thereon a cam 92 which is rotated by a pivot lever 96 (FIG. 3). A spacer 97 on either side of the cam 92 separates the cam from the head of the screw 93 and from the basket clamp 91. When the pivot lever 96 is pulled to its upward position (FIG. 6), the cam 92 presses the foot portion of the clamp 91 downward from the phantom position to the solid-line position shown in FIG. 4 thereby clamping the end of panel 60 tightly against the floor of the bracket 72.

The clamp mechanism at the head end (the motor-drive end) is similar to that illustrated in FIGS. 4 and 6 and just described. At the head end, the clamp is 81, the cam 82, the pivot lever 86, the screw 83, the basket end bracket 52, and the bumper retainer 54.

The three components 50, 60 and 70 of the infant-receiving basket are readily assembled and disassembled. To assemble the components, a panel 60 of desired length is selected and one end, for example, the head end, is then inserted into the head section 50 by sliding the end of the panel 60 on to the floor of end bracket 52 under the clamp 81. The lever 86 is then pivoted manually through approximately 90° to cam the clamp 81 downwardly so that it presses tightly against the end of the panel 60. The foot end section, i.e., the basket section 70 and housing 30 is then moved into position so that the right end of the panel 60 is received on the floor of end bracket 72 below the clamp 91. The lever 96 is then pivoted manually through about 90° to cam the clamp 91 downwardly to lock the end of the panel in place. This completes the assembly of the infant basket.

The assembled infant-receiving basket is then placed in desired position, which in the case now being described, is on the stationary X-ray examination table top T, and the four levers 102 of the four suction feet 100 are pressed downwardly from upright positions to the down positions illustrated in FIGS. 1-3. This clamps the suction feet 100 to the table top T.

The means by which the suction feet 100 are connected to the infant-basket assembly will now be described. As seen in FIGS. 1 and 2, the cover plates 12 and 32 of end housings 10 and 30 are each provided with a pair of ears, identified 18 and 38, respectively. Referring now to FIG. 6, which is a view looking toward the foot end, it will be seen that secured, as by thumb screw 115, to each of the ears 38 is an upright mounting bracket 110 having a series of central holes 114 at different levels for receiving the thumb screw. On either side of each of the center screw holes 114 is a pair of holes 111 for receiving stabilizing pins. Such pins 112 are shown in FIG. 7. The lower end of the mounting bracket 110 has a center hole for receiving the screw 117 which is received within a boss welded to the upper body of the suction foot 100, thereby securing the mounting bracket 110 to the suction foot 100. A stabilizing pin 118 prevents pivotal movement between bracket 110 and suction foot 100.

Reference is now made to FIGS. 8-11 which show the infant-receiving basket attached to an adult-receiving basket. This is the combination which provides extreme versatility of position of the infant for X-ray examination purposes. The adult-receiving basket may preferably be similar to that described in my U.S. Pat. No. 3,757,129. Since the adult patient basket and its motor drive are fully described in my said patent, it will not be necessary to repeat the description here.

Figure 8:
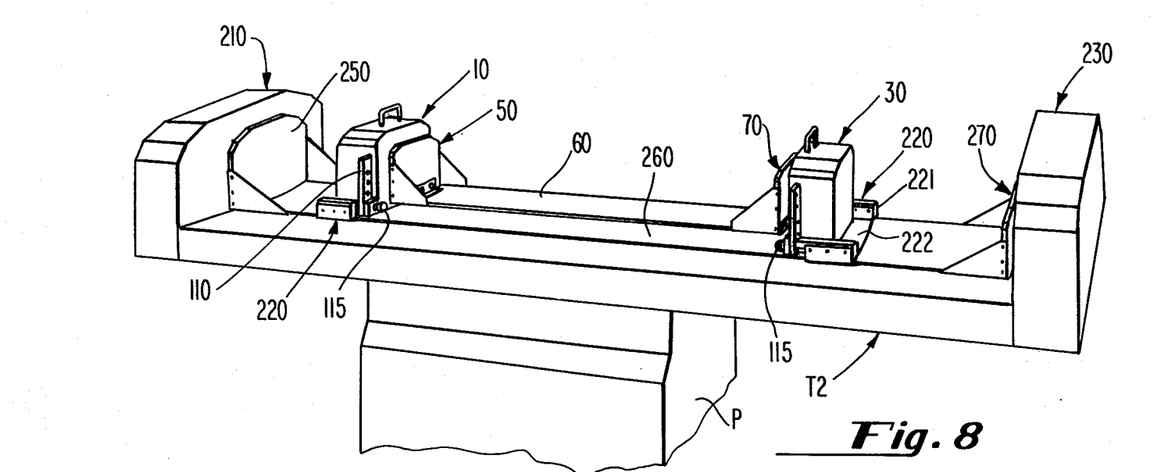
FIG. 8 is a perspective view showing the rotatable infant-receiving basket attached to a rotatable adult-receiving basket mounted on an X-ray examination table top supported on an elevator pedestal.
Figure 9:
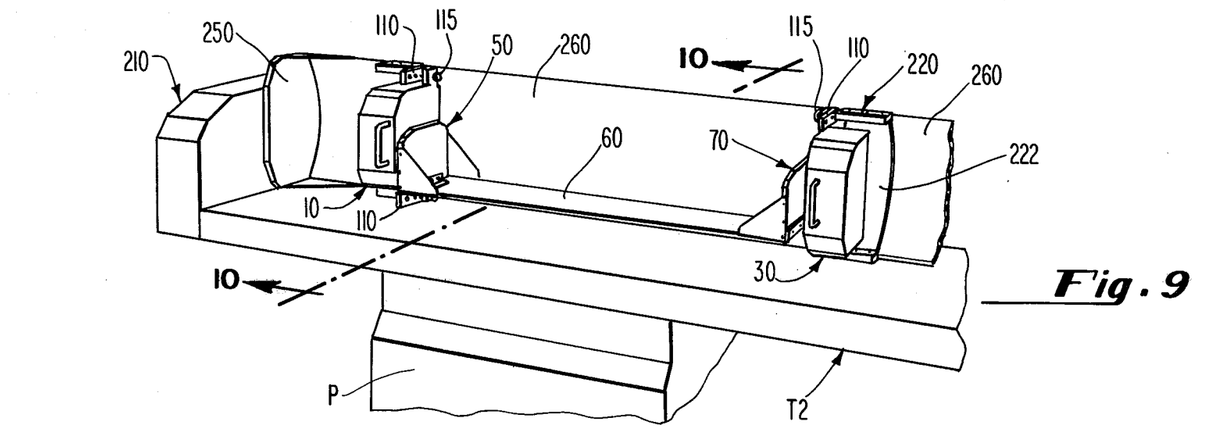
FIG. 9 is a perspective view of a portion of FIG. 8 showing the adult patient-receiving basket rotated counterclockwise 90° to a substantially vertical position with the infant-receiving basket rotated by its drive 90° in the opposite or clockwise direction, thereby to maintain the infant support panel in horizontal position for on-the-back X-ray examination without having the X-rays pass through the adult support panel.

In FIGS. 8 and 9, the adult-receiving basket is shown to include a head end 250, a patient-supporting arcuate or dished center panel 260, and a foot end 270. The basket end plates of ends 250 and 270 are mounted for pivotal movement on trunnions or pivot shafts which project from the drive housings 210 and 230, respectively. These housings 210 and 230 are mounted on a table top T2, which in turn is mounted on a elevator pedestal P. The table top T2 may also be assumed to be tiltable about its short transverse axis, but the details thereof are not shown. The head and foot housings 210 and 230 may be assumed to contain drives similar to those shown in my U.S. Pat. No. 3,757,129. These drives are adapted for rotating the adult basket about its longitudinal axis, and for moving the adult basket transversely.

For the purpose of attaching the infant-basket to the adult basket, there are provided, at spaced-apart locations on adult center panel 260, two cradle mounts 220 having bands 222 which span and embrace the adult panel 260. Cradle mounts 220 include, at each side of the panel 260, a horizontal bracket 221, shown in enlarged section in FIG. 11, having therein a horizontal hole 223 for receiving the horizontal shaft 116 of a vertically disposed mounting bracket 110. Shaft 116 is secured to mounting bracket 110 by screw 117. Mounting bracket 110 is identical in form to mounting brackets 110 used in the suction foot type of mounting shown in FIGS. 1-7.

Figure 10:
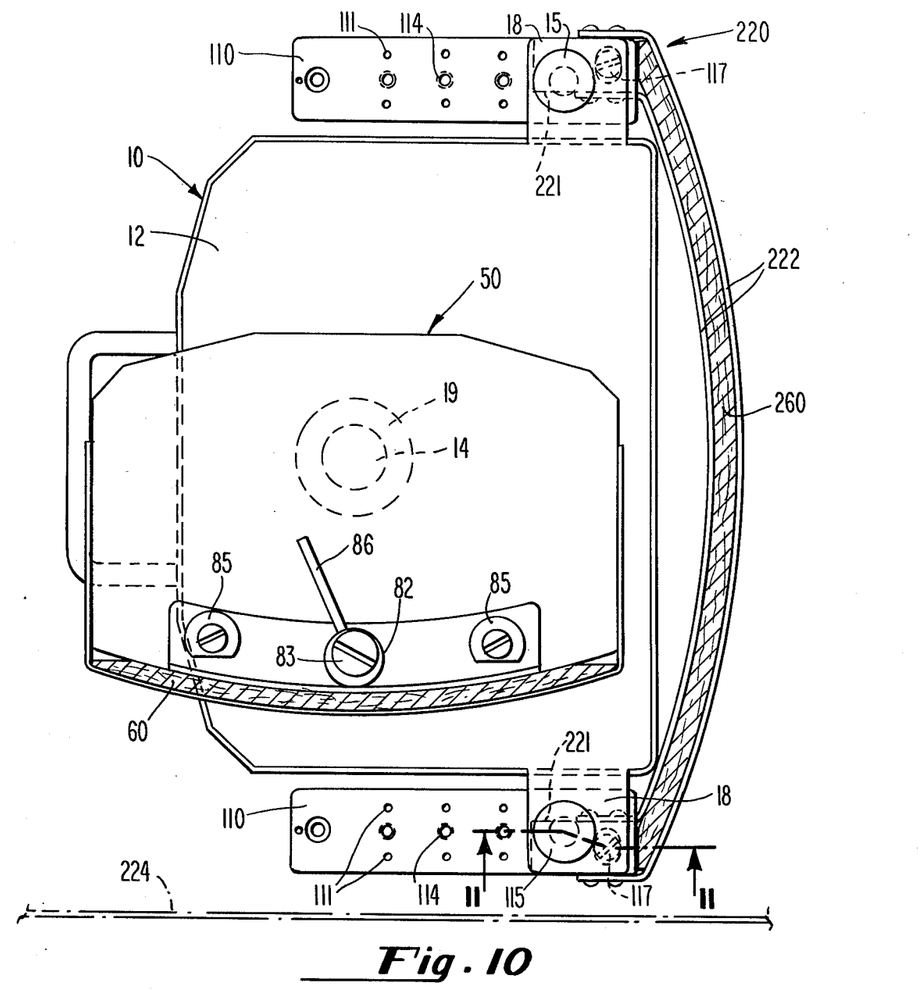
FIG. 10 is an elevational view looking toward the left along the line 10—10 of FIG. 9.
Figure 11:
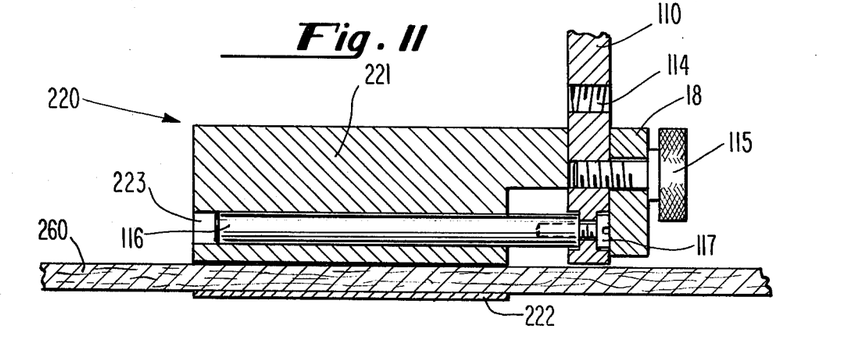
FIG. 11 is a detailed view looking down along the line 11—11 of FIG. 10.

As seen in FIGS. 10-11, thumb screws 115 attach the ears 18 of the end plate 12 of housing 10 to the mounting bracket 110 at a desired level. The slidable feature of cradle mounts 220 lengthwise along the adult panel 260 is of course used for entry of shaft 116 into hole 223 of bracket 221 at each side during the attachment operation. The slidable feature also allows for attachment of infant baskets of different lengths to the adult panel 260. Stabilizing pins similar to pins 112 in FIG. 7 are also used in securing ears 18 and 38 to mounting brackets 110 in FIGS. 8-11 but the pins are not seen in the illustrations.

FIGS. 9-10 illustrate an advantage to be derived from attaching the infant cradle to the adult cradle which is in addition to the advantages of versatility of examining position. The additional advantage relates to the removal of the adult support panel from the X-ray path. In FIGS. 9-10, the adult basket has been rotated counterclockwise through 90°. This rotational movement of the adult basket carries the infant basket with it. If the infant basket is not also rotated, the infant will be in on-the-side position for X-ray examination and the X-rays will not pass through the adult-support panel 260. This is an advantage, as it removes the impedance of the plywood panel 260 from the X-ray path. By rotating the infant basket 90° clockwise to the position illustrated in FIGS. 9-10, the infant may be X-rayed in on-the-back position, again without having the X-rays pass through the adult panel 260. With the adult cradle in the 90° position illustrated in FIGS. 9-10, the baby basket may, of course, be rotated to any angular position. While not illustrated in the drawings, the infant panel 60 may be provided with cut-outs to allow for barium enemas and milagrams. Since the adult cradle is movable in the transverse direction relative to the table top T2, the infant may be carried by the adult panel to any desired lateral position. Also, since the table top T2 may be elevated by the pedestal P, or may be tilted about its short transverse axis, the infant in an infant-cradle attached to an adult cradle may be placed in an extremely wide variety of positions for X-ray examination. Thus, the combination of infant basket and adult basket, illustrated in FIGS. 8-11 and the ease with which the infant basket may be attached and removed, makes an extremely attractive combination from a practical point of view.

A third type of mounting for the infant cradle is illustrated in FIGS. 12 and 13. The form of mounting is adapted for attaching the infant cradle to a table top T1 which is tiltable about its transverse axis, in contrast to the stationary table top T illustrated in FIGS. 1-7. Where the tiltable table top is to be used to place the infant in any angular position between horizontal and vertical, it would be unsafe to rely on the suction foot type of mounting shown in FIGS. 1-7. Accordingly, a more secure type of mounting is provided in FIGS. 12 and 13. In FIGS. 12 and 13, angle brackets 202 are secured by thumb screws 203 to the accessory sides rails 201 of the tiltable table top T1. Welded to the horizontal leg of angle bracket 202 is a cylindrical shaft 204 which is received within the sleeve shaft 205 of a mounting bracket 110. The sleeve shaft 205 is welded to the lower end of an upright bracket 110 which is similar in form to bracket 110 used in FIGS. 1-7 and also FIGS. 8-9. The brackets 110 are secured to the ears 18 of the cover plate 12 of housing 10 by the screws 115. Stablizing pins 112 project from the ears 18 and are received in holes 111 of the brackets 110. The attachment at the other end of the infant basket to ears 38 of plate 32 of housing 30 is by means identical to that just described.

In FIGS. 3 and 5, I have illustrated, and I have described, a motor drive for rotating the infant basket. Not shown and described are the control switches for operating the motor in the desired direction. Such controls are well known. Moreover, a remote control box may be provided. While the motor drive has been described as being at the head end of the cradle, it could, of course, be at the foot end.

While a motor drive is a more desirable form, in those cases where infrequent use of the infant basket is contemplated, and financial economy is a factor, the drive housing 10 may be modified to accommodate a hand crank connected to the worm shaft for turning the worm shaft manually. Preferably, the hand-crank driven worm shaft may be disposed at an angle rather than vertically as in FIGS. 3 and 5.

It will be seen from the foregoing description that the infant cradle system provided by the present invention has the ability to quickly and conveniently turn existing X-ray or treatment room equipment into small people pediatric equipment, without total dedication of space and equipment for small people. The pads and strap systems for holding the infant have not been illustrated.

What is claimed is:
1. An infant basket assembly for X-ray examination, said assembly comprising:
  a. an infant basket having:
    a-1 head and foot upright end sections;
    a-2 an infant-supporting center panel spanning between said end sections;

a-3 clamp means at each end section for detachably securing said end sections to opposite ends of said center panel, said clamp means including manually operable lever cam means for moving said clamp into and out of clamping position;

a-4 a pivot shaft extending axially outwardly from each end section;

a-5 support means for each pivot shaft;

a-6 drive means connected to one of said pivot shafts for driving said one pivot shaft rotationally;

b. attachment means for attaching said support means to table-top X-ray examination means.

2. An infant basket assembly for X-ray examination, said assembly comprising;

a. an infant basket having:

a-1 head and foot upright end sections;

a-2 an infant-supporting center panel spanning between said end sections;

a-3 clamp means at each end section for detachably securing said end sections to opposite ends of said center panel;

a-4 a pivot shaft extending axially outwardly from each end section;

a-5 support means for each pivot shaft;

a-6 drive means connected to one of said pivot shafts for driving said one pivot shaft rotationally;

b. attachment means for attaching said support means to table-top X-ray examination means which includes an adult-patient X-ray examination basket having an adult-supporting panel, said adult basket being rotatable separately and independently of said rotatable infant basket, said attachment means comprising means embracing and slidable along the adult-supporting panel for removably securing said pivot shaft support means to said adult-supporting panel.

3. Apparatus according to claim 1 wherein said drive means includes:

a. a reversible electric motor;

b. a worm shaft connected to and adapted to be driven by said motor;

c. a worm gear connected to and adapted to be driven by said worm;

d. said worm gear being mounted on and secured to said one pivot shaft.

4. Apparatus according to claim 3 wherein there is provided an adult-patient X-ray examination basket having an adult-supporting panel, said adult basket being rotatable separately and independently of said rotatable infant basket, and wherein said attachment means comprises:

a. means embracing and slidable along the adult-supporting panel for removably securing said pivot shaft support means to said adult-supporting panel.

5. Apparatus according to claim 3 wherein there is provided a tiltable table top having accessory side rails, and said attachment means comprises:

a. bracket means for removably securing said pivot shaft support means to said accessory side rails of a tiltable table top.

6. Apparatus according to claim 3 wherein there is provided a flat table top and said attachment means comprises:

a. suction-foot means;

b. bracket means for removably attaching said suction-foot means to said pivot shaft support means;

c. said suction-foot means being attachable to said table top.

7. Apparatus according to claim 2 wherein said pivot shaft support means includes:

a. a housing having a cover plate having laterally projecting ears;

b. bracket means connect said ears to said embracing slidable means.

* * * * *